United States Patent [19]

Davidson

[11] Patent Number: 4,814,480

[45] Date of Patent: Mar. 21, 1989

[54] TRIFLUOROMETHYLATION PROCESS

[75] Inventor: Robert I. Davidson, Baton Rouge, La.

[73] Assignee: Ethyl Corporation, Richmond, Va.

[21] Appl. No.: 854,085

[22] Filed: Apr. 21, 1986

[51] Int. Cl.$^4$ .................... C07C 120/00; C07C 51/00; C07C 21/24

[52] U.S. Cl. .................................. 558/378; 560/100; 570/144

[58] Field of Search ....................... 570/144; 560/100; 558/423, 378

[56] References Cited

U.S. PATENT DOCUMENTS 4,439,617  3/1984  Sestanj et al. ...................... 558/415

Primary Examiner—Anton H. Sutto
Attorney, Agent, or Firm—Patricia J. Hogan

[57] ABSTRACT

Trifluoromethylaromatic compounds are prepared by reacting the corresponding aromatic bromide or iodide with a tetraalkylammonium trifluoroacetate in the presence of cuprous iodide and a dipolar aprotic solvent.

20 Claims, No Drawings

TRIFLUOROMETHYLATION PROCESS

FIELD OF THE INVENTION

This invention relates to trifluoromethylaromatic compounds and more particularly to a process for preparing them.

BACKGROUND

As disclosed in Matsui et al., *Chemistry Letters*, 1981, pp. 1719–1720, it is known that aromatic iodides can be trifluoromethylated by reacting them with a large excess of sodium trifluoroacetate in the presence of cuprous iodide and a dipolar aprotic solvent. Matsui et al. also show that some trifluoromethylation occurs when an aromatic bromide is employed in the reaction instead of an iodide but that the yield of product is quite low.

Copending U.S. patent application Ser. No. 724,474 (Ramachandran et al.), filed Apr. 18, 1985, now U.S. Pat. No. 4,590,010, teaches that the technique of Matsui et al. is applicable to the trifluoromethylation of 6-alkoxy-5-halo-1-cyanonaphthalenes and the corresponding naphthoate esters—compounds which, like the compounds of Matsui et al., give better yields of the desired products when the halo substituent is iodo. Ramachandran et al. indicate that other trifluoroacetate salts can be used in their process, but they disclose a preference for using sodium trifluoroacetate as the trifluoromethylating agent.

Copending U.A. patent application Ser. No. 808,304 (Lin et al.), filed Dec. 12, 1985, teaches that potassium trifluoroacetate is more selective than sodium trifluoroacetate, can be used in smaller amounts, and does not require as long a reaction time when it is used to trifluoromethylate an aromatic bromide or iodide. Moreover, in contrast to the known processes utilizing the sodium salt, trifluoromethylations using the potassium salt can permit the products to be obtained in high yields even when the starting materials are aromatic bromides.

SUMMARY OF THE INVETNION

An object of this invention is to provide a novel process for preparing trifluoromethylaromatic compounds.

Another object is to provide such a process wherein the trifluoromethylaromatic compounds can be prepared in high yields from aromatic iodides or aromatic bromides.

A further object is to provide such a process which utilizes a trifluoromethylating agent that is more selective than sodium trifluoroacetate, can be used in smaller amounts, and does not require as long a reaction time.

These and other objects are attained by reacting an aromatic bromide or iodide with a tetraalkylammonium trifluoroacetate in the presence of cuprous iodide and a dipolar aprotic solvent.

DETAILED DESCRIPTION

Aromatic halides utilizable in the practice of the invention are substituted and unsubstituted aromatic iodides and bromides wherein any substituents are inert substituents (i.e., substituents that do not prevent the reaction from occurring) such as alkyl, alkoxy, alkylthio, aryl, aryloxy, arylthio, cyano, nitro, acylamino, alkylamino, tertiary amino, sulfonamido, sulfone, sulfonyl, phosphino, perfluoroalkyl, chloro, fluoro, ester, aldehyde, ketone, acetal, sulfono groups, etc., and the aromatic ring may be a carbocyclic ring such as a benzene, naphthalene, anthracene, etc., ring or a five- or six-membered heterocyclic ring having aromatic character, e.g., a pyridine, quinoline, isoquinoline, thiophene, pyrrole, furan, etc., ring. Exemplary of such compounds are iodobenzene, 3-iodotoluene, 4-chloroiodobenzene, 4-iodomethoxybenzene, 1-iodonaphthalene, 3-iodoaniline, 1-iodo-3-nitrobenzene, 2-iodothiophene, 4-iodoisoquinoline, 2-iodopyridine, 3-iodoquinoline, the corresponding bromides, etc.

In a preferred embodiment of the invention, the aromatic halide is a halonaphthalene corresponding to the formula:

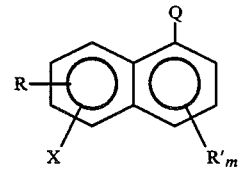

wherein R and R' are independently selected from chloro, fluoro, nitro, hydroxy, and alkyl and alkoxy substituents containing 1–6 carbons; Q is —CN or —COOR''; R'' is saturated hydrocarbyl; X is bromo or iodo; and m is 0 or 1.

The halocyanonaphthalenes and halonaphthoates utilizable in the practice of the invention may be any compounds corresponding to the above halonaphthalene formula, but they are preferably compounds wherein m is 0, X is in the 5-position, and R is an alkyl or alkoxy substituent in the 6-position. When the R and R' substituents are alkyl or alkoxy, they are generally straight-chain groups of 1–3 carbons or branched-chain groups of three or four carbons, such as methyl, ethyl, propyl, 1-methylethyl, butyl, 2-methylpropyl, 1,1-dimethylethyl, the corresponding alkoxy groups, etc., although, as indicated above, larger groups such as hexyl and hexoxy are also utilizable. When the halonaphthalene is an ester, R'' may be any saturated hydrocarbyl group (i.e., a hydrocarbyl group that is free of aliphatic unsaturation) but is preferably an alkyl, cycloalkyl, aryl, alkaryl, or aralkyl group containing 1–10 carbons, e.g., methyl, ethyl, propyl, cyclohexyl, phenyl, tolyl, benzyl, etc. Particularly preferred halonaphthalenes are 6-alkoxy-5-bromo-1-cyanonaphthalenes, 6-alkoxy-5-iodo-1-cyanonaphthalenes, 6-alkoxy-5-bromo-1-naphthoates, and 6-alkoxy-5-iodo-1-naphthoates, especially those compounds wherein the alkoxy groups are methoxy.

The halonaphthoates are known compounds. The halocyanonaphthalenes are compounds that can be prepared by cyanating the appropriately substituted tetralone, e.g., 6-methoxytetralone, to form the appropriately substituted 1-cyano-3,4-dihydronaphthalene, e.g., 6-methoxy-1-cyano-3,4-dihydronaphthalene, aromatizing the product in any suitable manner, and brominating or iodinating the resultant substituted 1-cyanonaphthalene by known techniques.

The tetralkylammonium trifluoroacetate may be any such compound wherein the alkyl groups, which may be the same or different and may be straight-chain or branched, contain about 1–20 carbons, generally about 1–12 carbons. Exemplary of such compounds are the tetramethyl, tetraethyl, tetrapropyl, tetrabutyl, tetrapentyl, tetrahexyl, tetraheptyl, methyltributyl, methyltrioctyl, methyltrialkyl($C_8$–$C_{10}$), butyltripropyl, heptyltriethyl, octyltriethyl, dodecyltrimethyl, dodecyltriethyl, tetradecyltrimethyl, and hexadecyltrimethylammonium trifluoroacetates, etc. The preferred trifluoroacetates are those wherein the alkyl groups contain about 1-6 carbons, especially tetramethylammonium trifluoroacetate. When not available, the tetralkylammonium trifluoroacetates may be prepared by reacting trifluoroacetic acid with a carbonate, hydroxide, or other salt of the appropriate amine or amines.

The amount of tetraalkylammonium trifluoroacetate reacted with the aromatic halide is not critical and may be a considerable excess, such as the amounts of sodium trifluoroacetate that have been employed in the past. However, since such large amounts of tetraalkylammonium trifluoroacetate are not required, the amount used is generally in the range of about 1-3 equivalents, most commonly about 1.5-2 equivalents.

Dipolar aprotic solvents that may be utilized include, e.g., N-methylpyrrolidone, N,N-dimethylformamide, N,N-dimethylacetamide, hexamethylphosphoric triamide, dimethylsulfoxide, etc. The particular solvent employed does not appear to be critical except in the sense that it should have an appropriate boiling point for use at the reaction temperatures to be utilized, but the preferred solvents are N,N-dimethylformamide and N,N-dimethylacetamide. The solvent is used in solvent amounts, e.g., an amount such as to provide an organic solids concentration of up to about 15%.

The cuprous iodide may be employed in any suitable amount, generally an amount in the range of about 0.5-5 equivalents.

The reaction is conducted by combining the ingredients in any convenient order and heating them at a suitable temperature, conveniently reflux temperature, to accomplish the desired trifluoromethylation. Anhydrous conditions are preferably employed, and the temperature is generally in the range of about 130°-160° C., preferably about 140°-155° C.

After completion of the reaction, the product may be recovered by conventional techniques and/or subjected to further reactions to form derivatives. For example, products obtained by trifluoromethylating the preferred halocyanonaphthalenes and halonaphthoates can be subjected to reactions such as those taught by Sestanj et al. in U.S. Pat. No. 4,439,617. Thus, e.g., (1) a (trifluoromethyl)cyanonaphthalene or trifluoromethylnaphthoate prepared by the trifluoromethylation reaction may be hydrolyzed to the corresponding acid in the presence of a base such as sodium or potassium hydroxide, (2) the acid can be halogenated, e.g., by reaction with thionyl chloride, to form the corresponding acid halide, (2) the acid halide may be reacted with a saturated hydrocarbyl ester of an acid corresponding to the formula $ZNHCH_2COOH$ (e.g., methyl, ethyl, propyl, cyclohexyl, phenyl, tolyl, or benzyl sarcosinate, the corresponding esters of aminoacetic acids having other N-substituents containing 1-6 carbons, such as N-ethyl, N-propyl, etc.) to form an amide corresponding to the formula:

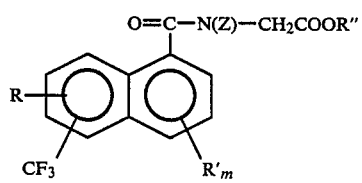

and (3) the amide may be thiated, e.g., with phosphorus pentasulfide or the like, and the product saponified and hydrolyzed to form a thioamide corresponding to the formula:

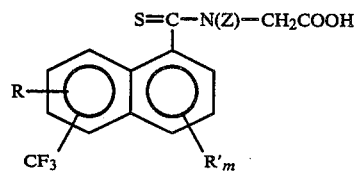

The invention is advantageous in that, like the potassium trifluoroacetate reaction of Lin et al., it permits trifluoromethylaromatic compounds to be prepared in high yields from the corresponding aromatic bromides or iodides at a faster rate and with the use of less reagent than is required when sodium trifluoroacetate is employed. Also, the reaction is more selective than the sodium trifluoroacetate reaction, so the product is less contaminated with by-products, such as the corresponding pentafluoroethyl compounds. Additionally, the tetraalkylammonium trifluoroacetate reactions can be accomplished with higher concentrations of solids than are operable when sodium trifluoroacetate is used, and the reactor productivity can thus be increased considerably.

The following examples are given to illustrate the invention and are not intended as a limitation thereof.

EXAMPLE I

A mixture of one molar proportion of 6-methoxy-5-bromo-1-cyanonaphthalene (MBCN), 1.5 molar proportions of tetramethylammonium trifluoroacetate (TMATA), and 2.1 molar proportions of CuI was stirred into 18 molar proportions of toluene, after which part of the toluene was stripped, 80 molar proportions of N,N-dimethylformamide (DMF) were added, and toluene and DMF were stripped until the temperature reached about 156° C. The reaction mixture was maintained at about 156° C. for two hours, cooled, worked up, and subjected to HPLC analysis. The analysis showed 87.1% by weight of 6-methoxy-5-trifluoromethyl-1-cyanonaphthalene (MTCN), 4.5% by weight of MBCN, and no 6-methoxy-5-pentafluoroethyl-1-cyanonaphthalene (MPCN).

EXAMPLE II

Example I was essentially repeated except that the TMATA was replaced with tetrabutylammonium trifluoroacetate. Due to the formation of some tetrabutylammonium bromide by-product, the HPLC analysis was normalized to show 82.3% by weight of MTCN, 8.5% by weight of MBCN, and no MPCN.

COMPARATIVE EXAMPLE

Example I was essentially repeated except that the TMATA was replaced with four molar proportions of sodium trifluoroacetate. The HPLC analysis showed 80.9% by weight of MTCN, only a trace of MBCN, and 4.9% by weight of MPCN.

It is obvious that many variations may be made in the products and processes set forth above without departing from the spirit and scope of this invention.

What is claimed is:

1. In a process for preparing a trifluoromethylaromatic compound by reacting an aromatic bromide or iodide with a trifluoroacetate in the presence of cuprous iodide and a dipolar aprotic solvent at a temperature of about 130°–160° C., the improvement which comprises employing a tetraalkylammonium trifluoroacetate as the trifluoroacetate.

2. The process of claim 1 wherein the aromatic halide is a bromide.

3. The process of claim 1 wherein the aromatic halide is an iodide.

4. The process of claim 1 wherein the aromatic halide is a halonaphthalene corresponding to the formula:

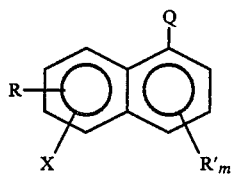

wherein R and R' are independently selected from chloro, fluoro, nitro, hydroxy, and alkyl and alkoxy substituents containing 1–14 6 carbons; Q is —CN or —COOR"; R" is saturated hydrocarbyl; X is bromo or iodo; and m is 0 or 1.

5. The process of claim 4 wherein the aromatic halide is a 6-alkoxy-5-bromo-1-cyanonaphthalene.

6. The process of claim 4 wherein the aromatic halide is a 6-alkoxy-5-bromo-1-naphthoate.

7. The process of claim 1 wherein the tetraalkylammonium trifluoroacetate is a compound in which the alkyl groups contain 1–20 carbons.

8. The process of claim 7 wherein the alkyl groups contain 1–12 carbons.

9. The process of claim 8 wherein the alkyl groups contain 1–6 carbons.

10. The process of claim 9 wherein the tetraalkylammonium trifluoroacetate is tetramethylammonium trifluoroacetate.

11. The process of claim 1 wherein the raction is conducted at about 140°–155° C.

12. The process of claim 1 wherein the aromatic halide is reacted with about 1–3 equivalents of the tetraalkylammonium trifluoroacetate.

13. The process of claim 1 wherein the solvent is N,N-dimethylformamide.

14. The process of claim 1 wherein the solvent is N,N-dimethylacetamide.

15. A process which comprises reacting a halonaphthalene corresponding to the formula:

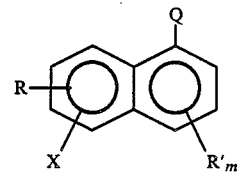

wherein R and R' are independently selected from chloro, fluoro, nitro, hydroxy, and alkyl and alkoxy substituents containing 1–6 carbons; Q is —CN or —COOR"; R" is saturated hydrocarbyl; X is bromo or iodo; and m is 0 or 1, with about 1–3 equivalents of a tetraalkylammonium trifluoroacetate in the presence of a dipolar aprotic solvent and about 0.5–5 equivalents of cuprous iodide at about 140°–155° C. so as to form a trifluoromethylaromatic compound.

16. The process of claim 15 wherin the solvent is N,N-dimethylformamide.

17. The process of claim 15 wherein the solvent is N,N-dimethylacetamide.

18. The process of claim 15 wherein the halonaphthalene is a 6-alkoxy-5-bromo-1-cyanonaphthalene.

19. The process of claim 15 wherein the halonaphthalene is a 6-alkoxy-5-bromo-1-naphthoate.

20. The process of claim 15 wherein the tetraalkylammonium trifluoroacetate is tetramethylammonium trifluoroacetate.

* * * * *

UNITED STATES PATENT AND TRADEMARK OFFICE
CERTIFICATE OF CORRECTION

PATENT NO. : 4,814,480

DATED : March 21, 1989

INVENTOR(S) : Robert I. Davidson

It is certified that error appears in the above-identified patent and that said Letters Patent is hereby corrected as shown below:

Column 1, line 30, reads "Copending U. A. patent" should read -- Copending application--.

Column 1, line 41, reads "Summary of the Invetnion" and should read -- Summary of Invention --.

Column 5, line 25, reads "1-14 6 carbons" and should read -- 1-6 carbons --.

Column 6, line 1, reads "the raction is" and should read -- the reaction is --.

Signed and Sealed this

Sixth Day of March, 1990

Attest:

JEFFREY M. SAMUELS

*Attesting Officer*  *Acting Commissioner of Patents and Trademarks*